United States Patent
Dewangan et al.

(10) Patent No.: US 7,234,355 B2
(45) Date of Patent: Jun. 26, 2007

(54) METHOD AND SYSTEM FOR INSPECTING FLAWS USING ULTRASOUND SCAN DATA

(75) Inventors: Sandeep Kumar Dewangan, Bangalore (IN); Anandraj Sengupta, Bangalore (IN); Amitabha Dutta, Bhubaneshwar (IN)

(73) Assignee: General Electric Company, Schenectady, NY (US)

(*) Notice: Subject to any disclaimer, the term of this patent is extended or adjusted under 35 U.S.C. 154(b) by 215 days.

(21) Appl. No.: 11/022,726

(22) Filed: Dec. 27, 2004

(65) Prior Publication Data

US 2006/0137451 A1    Jun. 29, 2006

(51) Int. Cl.
G01N 29/06 (2006.01)
G01N 29/40 (2006.01)
G01N 29/48 (2006.01)
G01N 29/11 (2006.01)

(52) U.S. Cl. .............................. 73/622; 73/623; 73/602
(58) Field of Classification Search ................. 73/622, 73/623
See application file for complete search history.

(56) References Cited

U.S. PATENT DOCUMENTS

| | | | |
|---|---|---|---|
| 3,436,958 A | | 4/1969 | Proctor |
| 3,608,363 A | | 9/1971 | Whittington |
| 3,766,775 A | * | 10/1973 | Gunkel .................. 73/623 |
| 4,187,725 A | | 2/1980 | Gavrev et al. |
| 4,226,122 A | * | 10/1980 | Lund et al. .............. 73/609 |
| 4,265,119 A | * | 5/1981 | Dubetz et al. ............... 73/588 |
| 4,428,235 A | * | 1/1984 | Sugiyama .................... 73/574 |
| 4,481,824 A | * | 11/1984 | Fujimoto et al. ............ 73/643 |
| 4,869,109 A | * | 9/1989 | Miglianico et al. .......... 73/602 |
| 5,675,084 A | | 10/1997 | Goedecke ..................... 73/623 |
| 6,243,657 B1 | | 6/2001 | Tuck et al. ................. 702/150 |
| 2002/0174722 A1 | * | 11/2002 | Bazarov et al. .............. 73/623 |
| 2003/0136195 A1 | | 7/2003 | Krieg et al. ................. 73/628 |

FOREIGN PATENT DOCUMENTS

| | | |
|---|---|---|
| EP | 2000193646 | 7/2000 |
| GB | 2380794 A | 4/2003 |
| JP | 2000193646 | 7/2000 |
| WO | WO 03/021249 A2 | 3/2003 |

OTHER PUBLICATIONS

Tucker, Raymond W., Jr., et al., Characterization of gas pipeline flaws using wavelet analysis, Sixth International Conference on Quality Control by Artificial Vision, Kenneth W. Tobin, Jr., Fabrice Mariaudeau Editors, SPIE, vol. 5132 (2003) SPIE 0277-786X/03, XP-002375883.

* cited by examiner

*Primary Examiner*—Hezron Williams
*Assistant Examiner*—Rose M. Miller
(74) *Attorney, Agent, or Firm*—Fletcher Yoder

(57) ABSTRACT

A method and system for detecting weld signatures from an ultrasound scan data obtained from scanning a pipeline is provided. The method includes a step for mapping multiple amplitude responses from the ultrasound scan data, each amplitude response being representative of a respective sensor signal. Continuous amplitude responses are located from the amplitude responses and corresponding signatures are identified for the continuous amplitude responses. The method also includes a step for tagging the corresponding signatures as weld signatures.

19 Claims, 7 Drawing Sheets

METHOD AND SYSTEM FOR INSPECTING FLAWS USING ULTRASOUND SCAN DATA

BACKGROUND

The invention relates generally to inspection systems and particularly to pipeline inspection systems that use ultrasound data for inspection of pipe flaws.

Pipelines are widely used in a variety of industries, allowing a large amount of material to be transported from one place to another. A variety of fluids such as oil and/or gas are transported cheaply and efficiently using pipelines. Particulate matter, and other small solids suspended in fluids may also be transported through pipelines. Underground and underwater (deep sea) pipelines typically carry enormous quantities of oil and gas products that are important to energy-related industries, often under high pressure and at extreme temperatures and at high flow rates.

Flaws in constituent pipes may cause pipeline integrity degradation as the pipeline infrastructure ages. Corrosion of a pipeline can be caused by small spots of weakness, subsidence of the soil, local construction projects, seismic activity, weather, and simply wear and tear caused by normal use, and can lead to defects and anomalies in the pipeline. Thus, flaws or defects and anomalies can appear in the surface of the pipeline in the form of corrosion, mechanical damage, fatigue, crack, stress, corrosion cracks, hydrogen induced cracks, or distortion due to dents or wrinkles.

Maintaining and protecting existing pipeline networks is proving to be a challenge. Current state-of-art inline inspection systems use Pipeline Inspection Gages (PIG). These acquire data from multiple sensors while the system travels inside the pipeline. A typical single run for the PIG may be more than 100 km long. The analysis of data and reporting of the findings is semi-automated. Current data analysis methods require on an average, about 200 man-days using ultrasound detection techniques to analyze and evaluate data from a 100 km long pipeline section. These techniques also result in high incidence of false positives because weld signatures (reflections from the weld interfaces of the pipeline) have very similar characteristics as cracks and notches and generally any feature recognition algorithm employed to extract flaws in the pipeline cannot easily distinguish between flaw signatures and weld signatures, which results in a high incidence of false calls.

Therefore there is a need for providing a method for removing weld and noise signatures from the ultrasound scan data obtained by inspecting a pipeline so that flaw signatures are retained for repair/maintenance follow-up activities.

BRIEF DESCRIPTION

Briefly in accordance with one aspect of the present technique, a method for detecting weld signatures from ultrasound scan data obtained from scanning a pipeline is provided. The method includes a step for mapping multiple amplitude responses from the ultrasound scan data, each amplitude response being representative of a respective sensor signal. Continuous amplitude responses are located from the amplitude responses and corresponding signatures are identified for the continuous amplitude responses. The method also includes a step for tagging the corresponding signatures as weld signatures.

In accordance with another aspect, an ultrasound imaging system used for detecting flaw signatures is provided. The system includes multiple sensors disposed around a region of interest and configured to transmit and receive signals from the region of interest. A data acquisition system is provided for acquiring ultrasound scan data from the sensors, the data being representative of signals received by the sensors from the region of interest. An amplitude processing component is also provided for mapping multiple amplitude responses from the ultrasound scan data, and for locating continuous amplitude responses, each amplitude response being representative of a respective sensor signal. A weld signature tagging and suppressing component is also provided for identifying corresponding signatures for the continuous amplitude responses and for tagging the corresponding signatures as weld signatures, and for suppressing the weld signatures and obtaining a weld-suppressed image.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The various aspects of the present technique deal with identifying and tagging of ultrasound signals reflected from lamination-like structures on parts. Though the aspects have been described in relation to pipeline applications where the lamination-like structure being addressed is a weld interface, the techniques described herein are equally applicable in other environments, for example, identifying flaws in rail tracks or planar flaws in sheets, rolls or plates. Aspects of the present technique are particularly advantageous as they serve to identify and remove all weld reflections from weld interfaces without removing any flaw signatures. The flaw signatures considered for retention may be, for example, cracks, notches, crack-fields, and combinations thereof.

Figure 1:
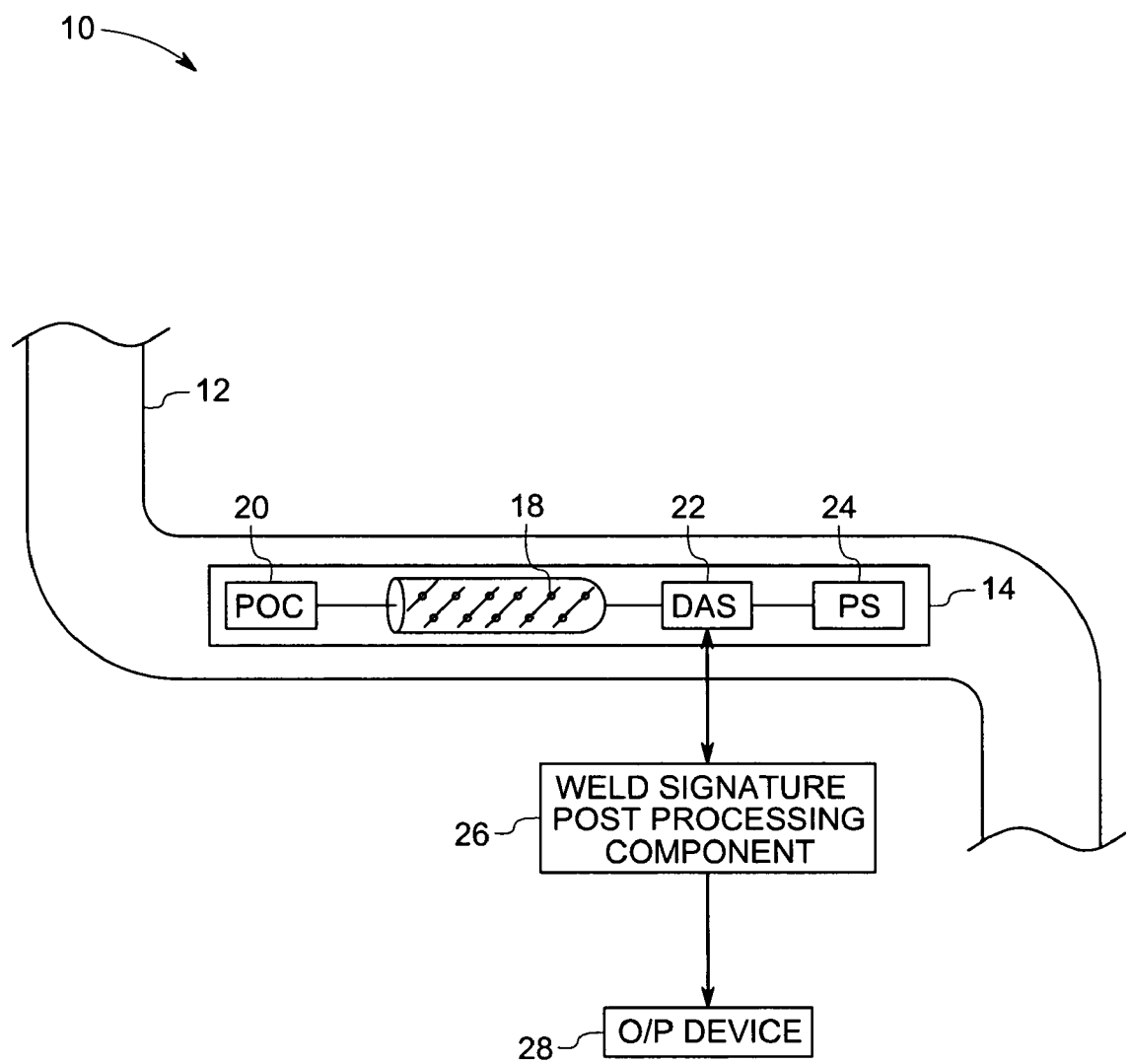
FIG. 1 is a block diagram showing a pipeline inspection system according to aspects of the present technique.

FIG. 1 is a diagrammatic representation of a pipeline inspection system, designated generally by reference numeral 10, that includes, a pipeline 12 and a pipeline inspection gage (PIG) 14. The PIG 14 is a scanning device placed inside the pipeline and is typically used to find flaws in the pipeline walls. The PIG is transported through the length of the pipeline with the fluid flow in the pipeline. The PIG is typically configured to send ultrasonic signals towards the pipeline walls and receives reflected signals from the pipeline walls. As shown in the FIG. 1, PIG 14 includes multiple sensors. Sensors 18 are typically transducers which function as transmitters and receptors of ultrasonic signals. Sensors may be piezoelectric sensors or other sensors commonly used for this type of application. The PIG 14 also includes a positional component (POC) 20, which determines the position and orientation of PIG in the pipeline. PIG further includes a data acquisition system (DAS) 22 for receiving the data acquired by the sensors 18. A power source (PS) 24 provides power to sensors, POC, DAS and other associated components in the PIG. It would be understood by those skilled in the art that PIG may have additional components such as an onboard clock for time stamping each record as acquired by the DAS or the like. Similarly, the pipeline inspection system may include additional components like magnetometers or magloggers, odometers and an off-board clock to record position and the overall distance traveled by the PIG. The pipeline inspection system 10 also includes a post-processing component 26 which may be incorporated inside the PIG or may be located remotely. The post processing component processes the scan data obtained from DAS for weld identification according to aspects of the present technique, as described in more detail in reference to FIG. 4-10. The pipeline inspection system may also be coupled to an output (O/P) device 28, for example an offline computer system for display of results from the post-processing component and for providing external inputs including user/operator inputs.

Figure 2:
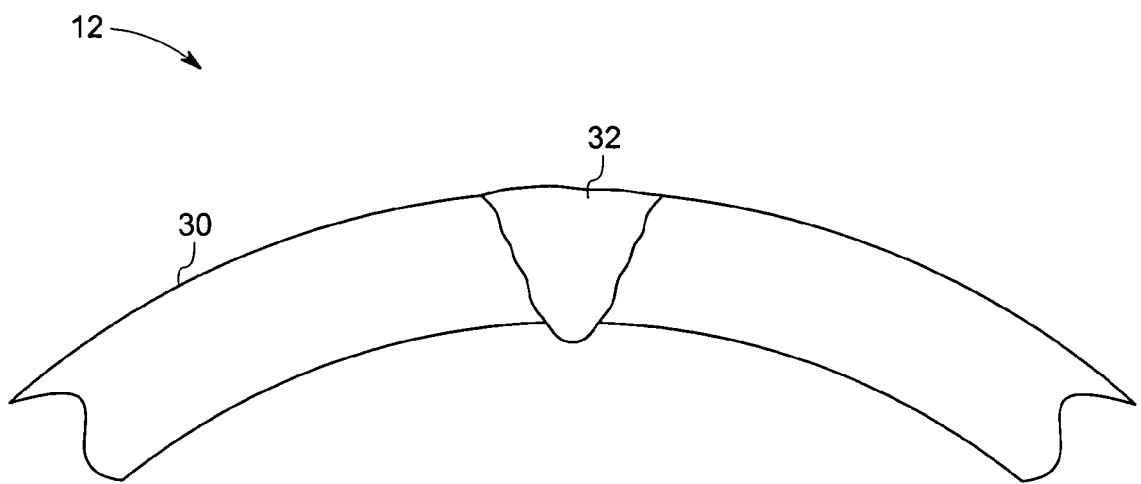
FIG. 2 is a cross-sectional view of a weld on a surface of the pipeline of FIG. 1.

FIG. 2 is a cross-sectional view of a weld 32 on a surface 30 of the pipeline 12. It will be well understood by those skilled in the art, that the presence of weld interfaces in the pipe wall cross section leads to reflections of the ultrasonic signal. The scan data from the PIG typically shows a very high concentration of high amplitude responses near longitudinal welds due to reflection of ultrasonic waves from these weld interfaces, and these responses have similarities with flaw signatures. As will be appreciated by those skilled in the art, though there are similarities between flaw and weld signatures, there are also inherent differences. Weld signatures are typically continuous, long, horizontal, and have uniform amplitude, where as flaw signatures are small, may or may not be horizontal, and the amplitude generally has a rise and a fall component along the length. These differentiating characteristics are employed in accordance with aspects of the present technique to detect weld signatures and suppress them to retain the actual flaw signatures, which may be used for maintenance or repair activities.

Figure 3:
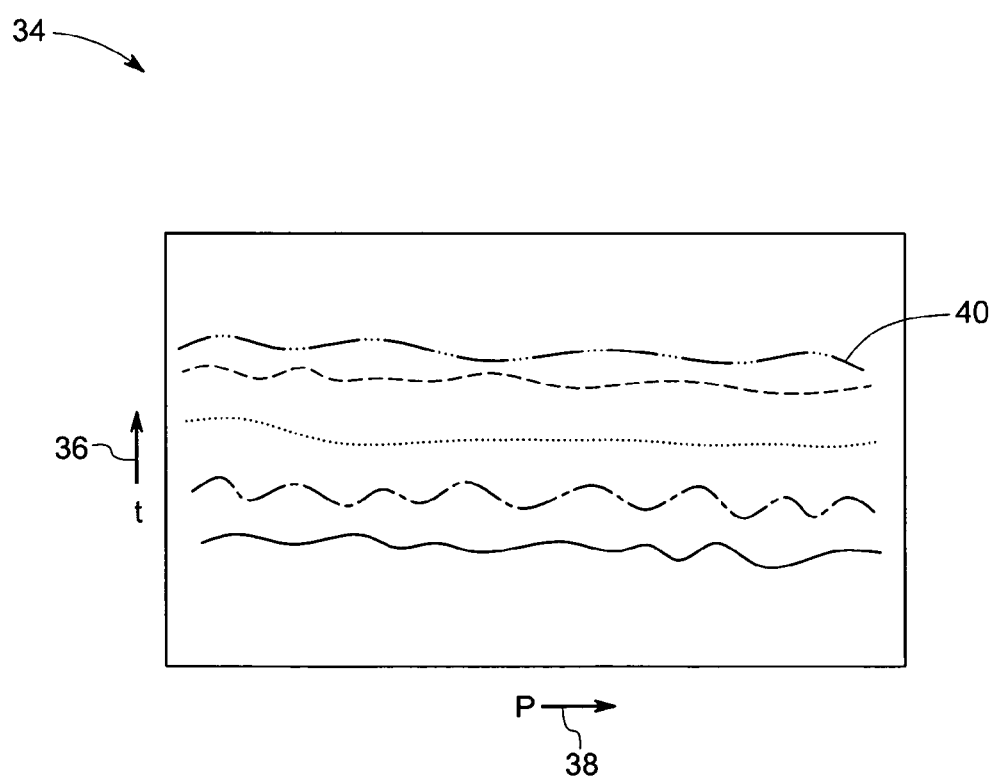
FIG. 3 is a graphical representation of exemplary scan data obtained from the pipeline inspection system shown in FIG. 1.

FIG. 3 is a graphical representation of exemplary scan data obtained from the pipeline inspection system shown in FIG. 1. The scan may be obtained from a portion of pipeline or similar structures, for example, a portion of rail, a portion of a sheet, or a portion of any planar structure. The portion may be a region of interest in some applications of the ultrasound modality. The scan shown in FIG. 3 is a B-scan which includes the received ultrasonic signals 40 (reflected signals) with respect to time-of-flight 36 of these signals and with respect to position 38 of the received signal 40.

Figure 4:
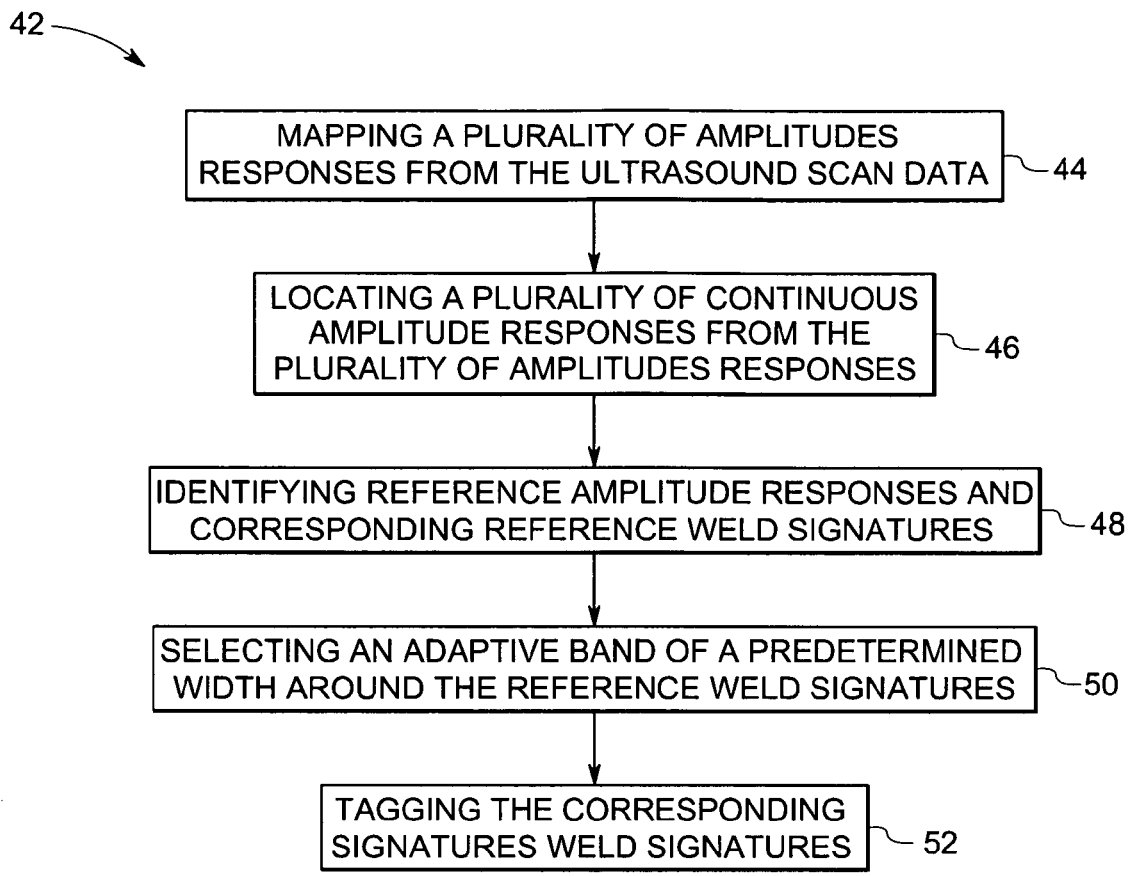
FIG. 4 is a flowchart showing exemplary steps for detecting weld signatures from an ultrasound scan obtained from scanning a pipeline.

FIG. 4 is a flowchart 42 illustrating one aspect of the present technique, for detecting weld signatures from the ultrasound scan data (ultrasound image) obtained from scanning the pipeline. The method includes a step 44 for mapping multiple amplitude responses from the ultrasound scan data, each amplitude response being representative of a respective sensor signal. The amplitudes of the suspected flaw signatures may be recorded in this step, with respect to, a distance traveled by the ultrasonic signal (time of flight), for a respective signature. At step 46, the method includes locating multiple continuous amplitude responses from the multiple amplitude responses of step 44. The continuous amplitude responses as described earlier, are an indicator of weld signatures. In one example, the continuous amplitude response is a highest amplitude peak from the multiple amplitude responses. In another example, the continuous amplitude response is the highest and longest amplitude peak. At step 48, the method includes identifying reference amplitude responses from the continuous responses and identifying corresponding signatures for the reference amplitude responses. Step 50 includes selecting an adaptive band of a pre-determined width around reference weld signatures (reference amplitude responses), and step 52 includes tagging the corresponding signatures in the adaptive band as weld signatures. These steps are described in more detail in reference to FIGS. 5-10. It would be well appreciated by those skilled in the art that the steps described herein in the different flowcharts may be functionalized through hardware or software. The hardware implementation may include in one example an apparatus for identifying weld signatures from an ultrasound scan data. The apparatus may be a part of the post-processing component 26 of FIG. 2 and is not shown separately. The apparatus may include an amplitude processing component for mapping a plurality of amplitude responses from the ultrasound scan data, and for locating a plurality of continuous amplitude responses, each amplitude response being representative of a respective sensor signal; and a weld signature tagging component for identifying corresponding signatures for the continuous amplitude responses and for tagging the corresponding signatures as weld signatures.

Figure 5:
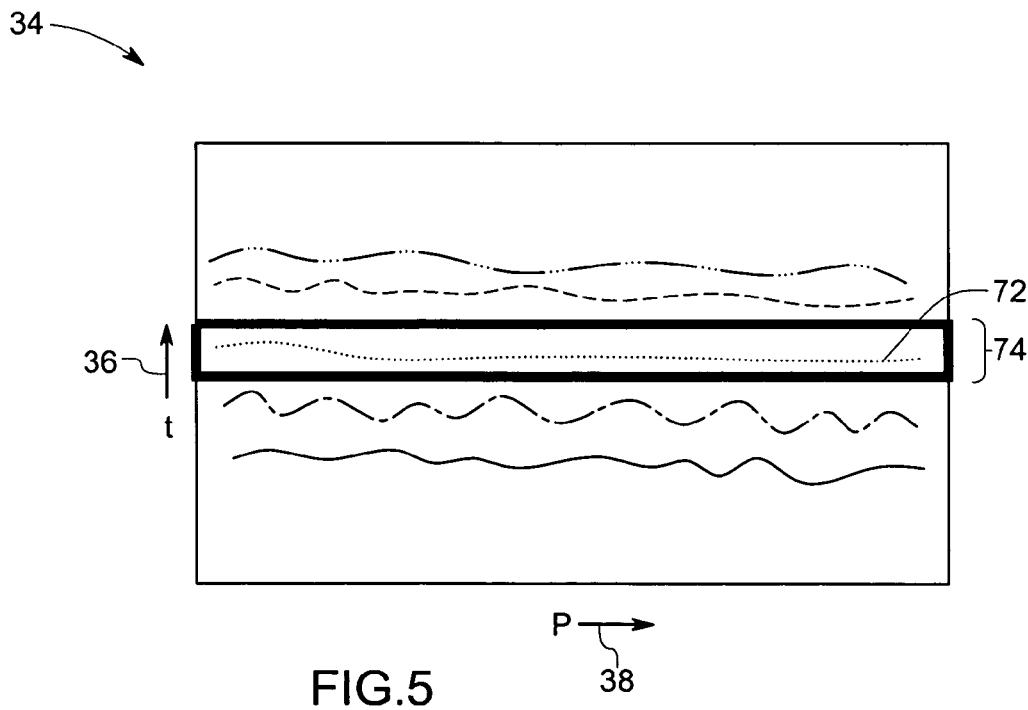
FIG. 5 is a graphical representation of exemplary scan data obtained from the pipeline inspection system shown in FIG. 1, including an illustrative window of pre-determined pixel-width.

FIG. 5 is a graphical representation of exemplary scan data 34 (time axis being indicated by reference numeral 36 and position axis being determined by reference numeral 40) obtained from the pipeline inspection system shown in FIG. 1, including an illustrative window 72 of pre-determined pixel-width 74. The window is rolled to cover the entire width of the scan and to capture the plurality of amplitudes as described in step 44 of FIG. 4. The pre-determined width selection may be a user input or it may be derived from the system as a feedback control input. The width may be variable or a fixed, depending on the end-use application.

Figure 6:
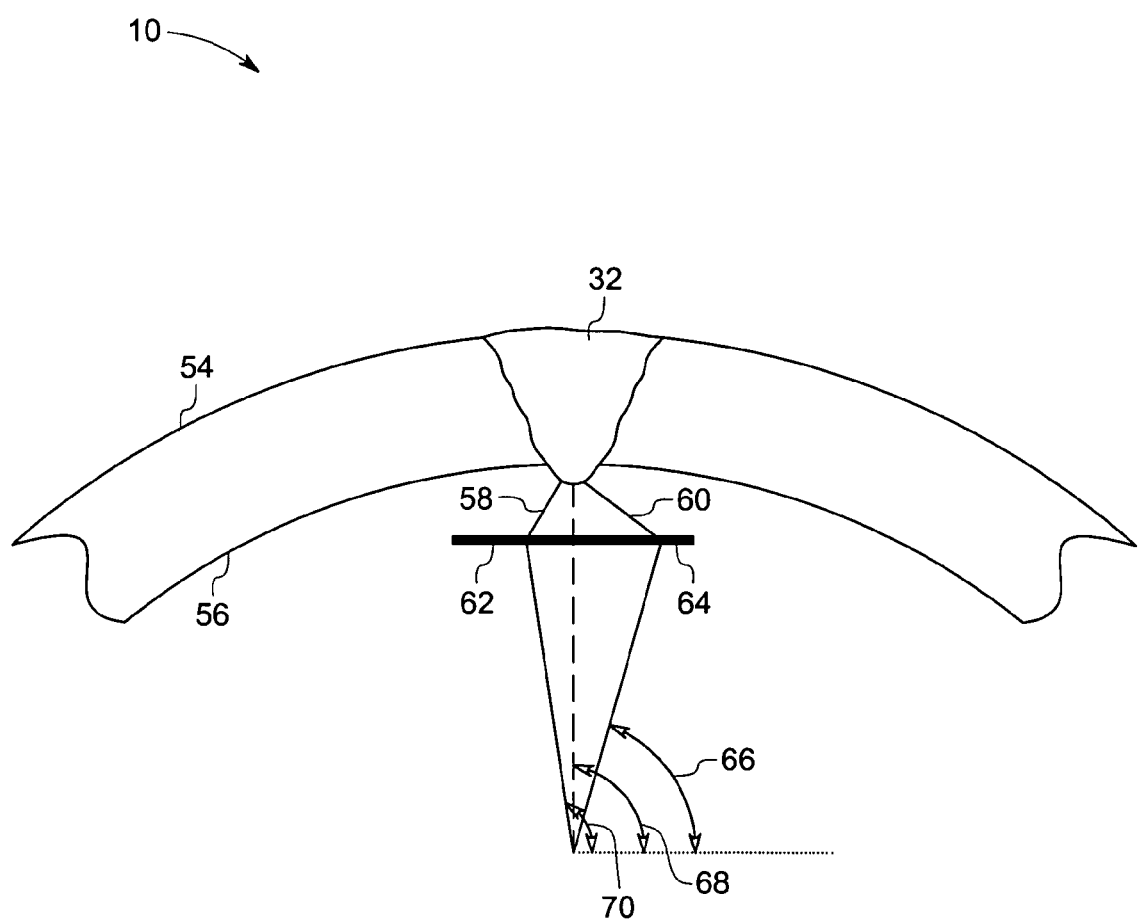
FIG. 6 is a diagrammatic representation of direct surface reflection signals from a weld in a surface of the pipeline.

FIG. 6 shows a diagrammatic representation of direct surface reflection signals 58, 60 from a weld 32 in the surface 54, 56 of a pipeline 10. Aspects of the present technique include automatic detection of a long weld angle co-ordinate 68 using the presence of direct surface reflection signals and attributes such as, length and time position of direct surface reflections. The long weld angle co-ordinate is generally used as a reference co-ordinate for tagging and physically locating any flaws in a pipeline. Hence accurate estimation of the long weld angle co-ordinate is extremely useful for pipeline inspection purpose. The direct surface reflection signals are characterized by long and continuous high amplitude signatures having a low time-of-flight. "Time of flight" as used herein means the distance traveled by the ultrasonic wave from the sensor to any surface from which the signal may be reflected and received back at the same sensor. For example, the distance from sensor 62 to the weld 32 and back to sensor 62 would be the time of flight for direct surface reflection signal 58. An amplitude filter may be used to extract amplitude responses for direct surface reflections and the sensor positions corresponding to these amplitude responses may be identified. For example, for the direct surface reflection signal 58, the angular position 70 of sensor 62 is identified. Typically in ultrasonic transmission, the neighboring sensors have trails of the direct surface reflection signal but at a higher time-of-flight. The sensor positions are also recorded for adjacent sensors (for example, for sensor 64, angular position 66 is identified). In the PIG, the sensors are generally arranged in adjacent pairs in clockwise (CW) and counter clockwise (CCW) direction. But the aspects of present technique are not limited to any particular orientation of the sensors. Actual long weld angle co-ordinate 68 may then obtained by picking the sensor angles seeing the longest surface weld reflections and taking their time-of-flight weighted average. A multi-parameter scoring may be used based on the presence, length and time position of direct surface reflection obtained from ultrasonic scans of the ultrasound image.

Figure 7:
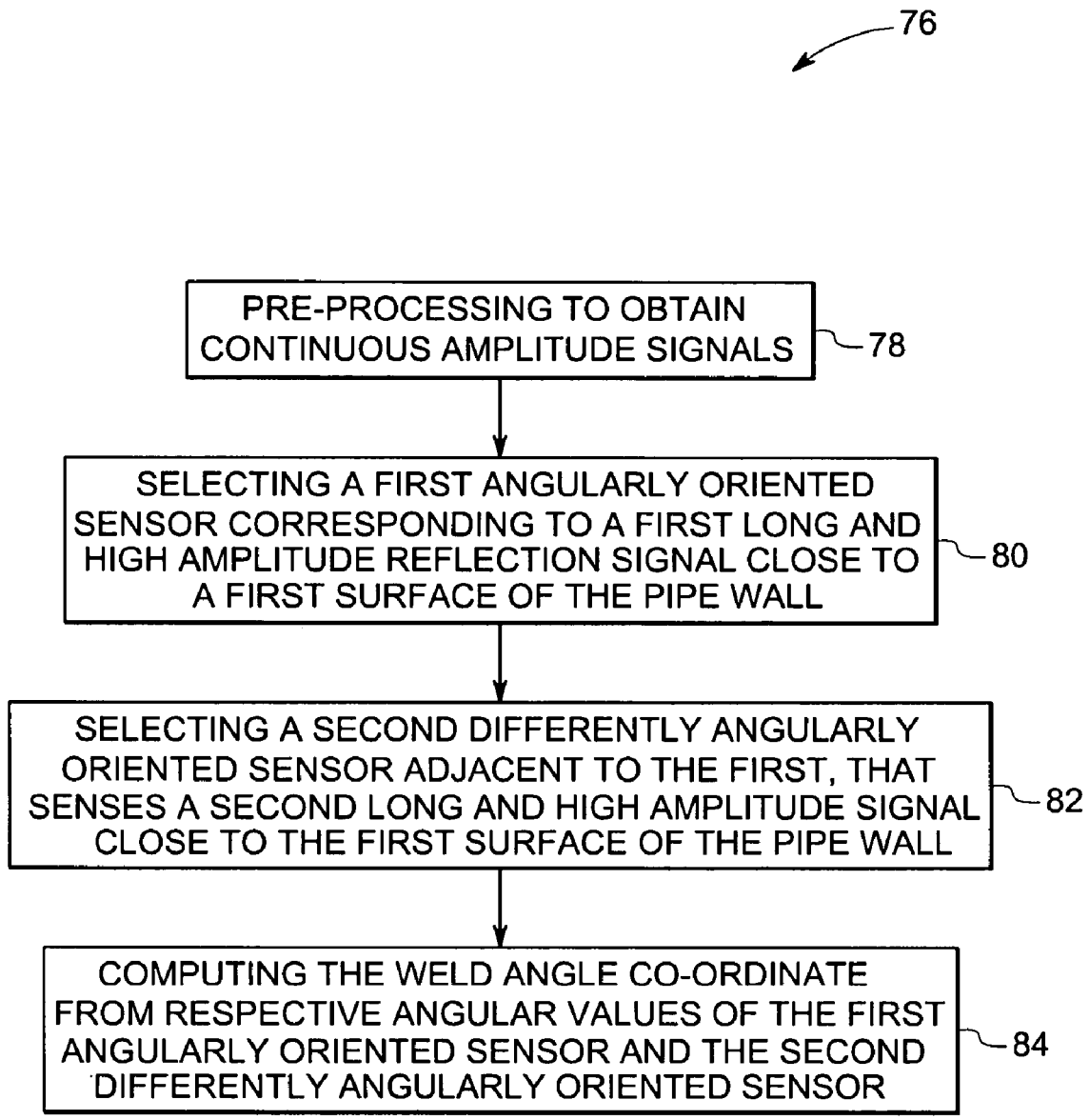
FIG. 7 is a flowchart showing exemplary steps for locating a long weld angle co-ordinate according to one aspect of present technique.

FIG. 7 is a flowchart 76 illustrating exemplary steps for locating a long weld angle co-ordinate as described in reference to FIG. 6. A step 78 includes preprocessing the scan data to filter high amplitude signals and performing edge-linking to connect points to obtain a direct weld surface reflection. Thus, in the pre-processing step 78, the broken weld surface signatures are connected, thereby forming a continuous line out of broken/discontinuous signal. The technique includes a step 80 for selecting a first angularly oriented sensor that senses a long and high amplitude reflection signal close to pipeline surface. At step 82, a second differently oriented sensor is selected (angle of orientation is different from first) adjacent to the first sensor that senses the long and high amplitude signal close to pipeline surface. At step 84, actual weld angle co-ordinate is obtained by computing the weld angle co-ordinate from respective angular values of the first angularly oriented sensor and the second differently angularly oriented sensor. Thus, the sensor angles with the longest surface weld reflections in each direction are recorded and their time-of-flight weighted average is computed to calculate the long weld angle co-ordinate.

Figure 8:
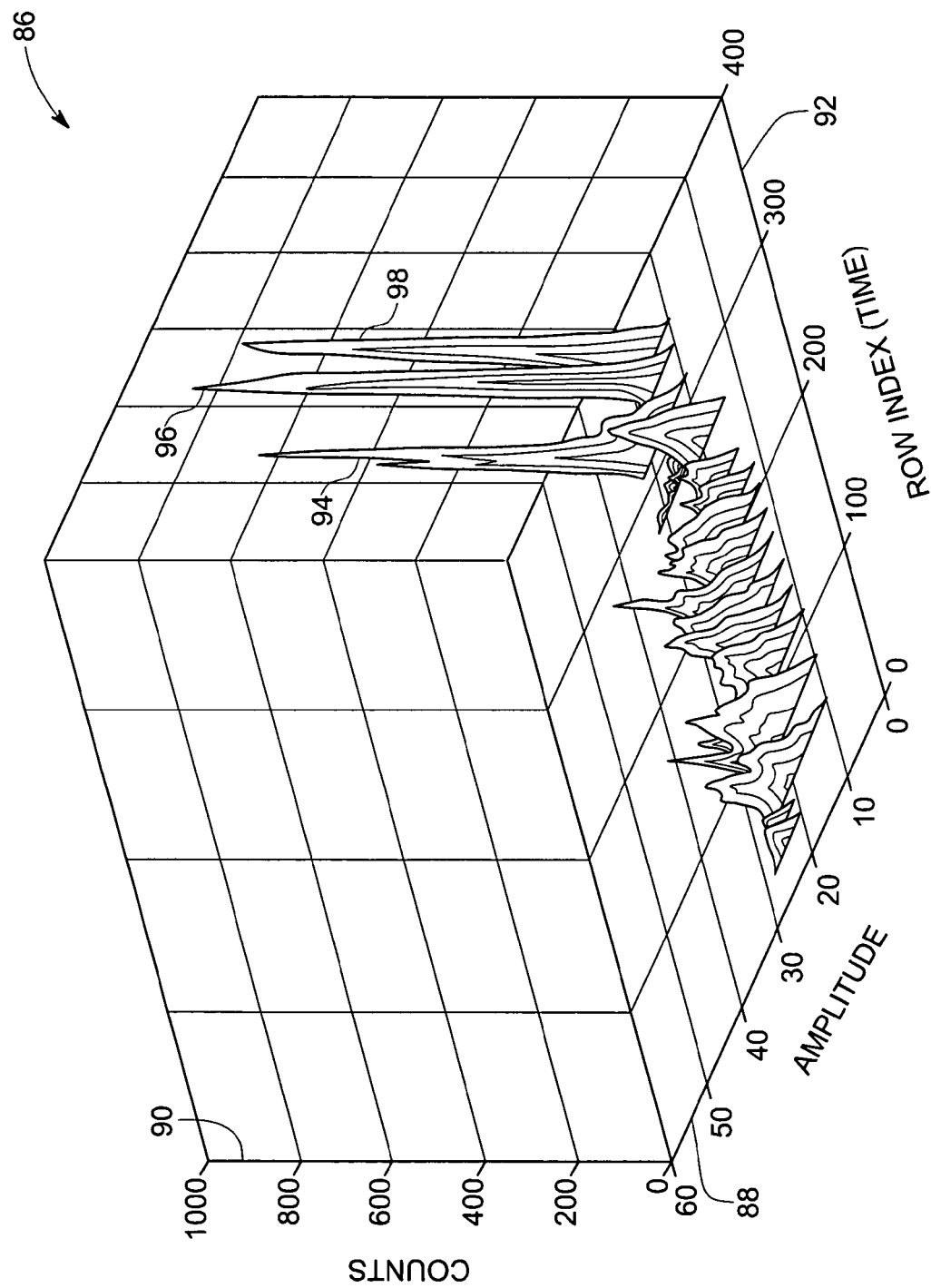
FIG. 8 is a diagrammatic representation of a three-dimensional histogram that may be used for mapping the signatures from the ultrasound scan data in accordance with aspects of the present technique.

In addition to locating the long weld angle co-ordinate, the aspects of present technique include a method to separate the weld signatures from actual flaw signatures even if the flaw is embedded within the weld. In an exemplary embodiment as shown in FIG. 8, all the signatures from the ultrasound scan data are mapped onto a three dimensional histogram 86. The three axes of the histogram designated generally by reference numerals 88, 90 and 92, being amplitude, number of counts (position) and time respectively, as shown in FIG. 8. Then, by using attributes like length, standard deviation of amplitude response, and its spatial deviation, as thresholds, high amplitude peaks 94, 96, 98 are located and identified as weld signatures, different from flaws. These aspects are described in more detail in reference to FIG. 9.

Figure 9:
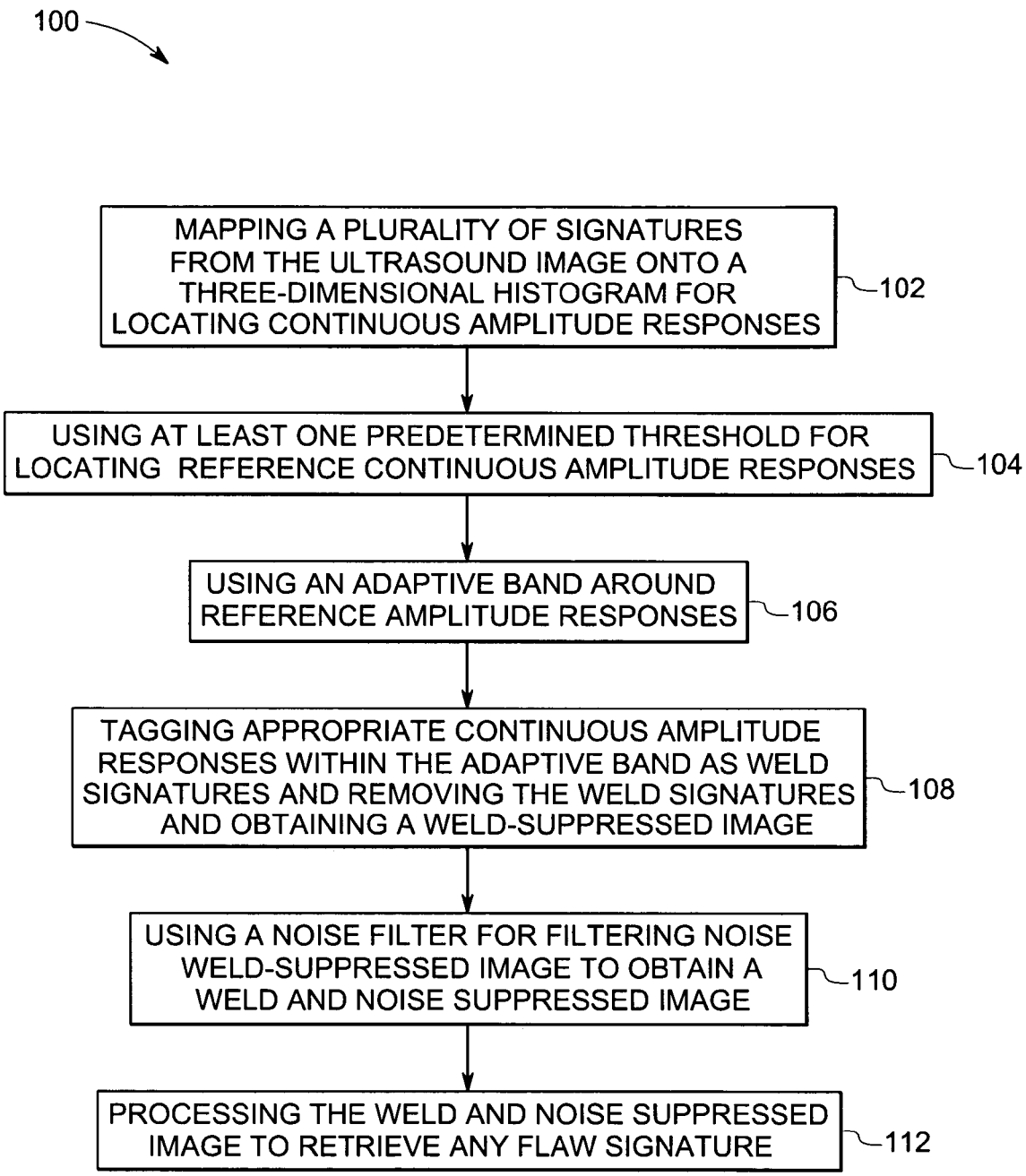
FIG. 9 is a flowchart showing exemplary steps for detecting, tagging and suppressing weld signatures and retaining flaw signatures according to one aspect of present technique.

FIG. 9 is a flowchart 100 illustrating exemplary steps for detecting and tagging weld signatures. At step 102, multiple amplitude responses from the ultrasound scan are mapped on a three dimensional histogram for locating continuous amplitude responses. At step 104, at least one pre-determined threshold is used for locating continuous amplitude responses. The pre-determined threshold is at least one of length, standard deviation or spatial deviation of the amplitude response. In one example a first threshold (Threshold 1 as given below) is chosen as the ratio of minimum length of weld signature to be filtered (user defined) to the maximum of the total length of the amplitude responses in the scan.

Threshold 1=(0.6*len)/(4×len)

Where len=maximum length of non zero columns within the scan
0.6=empirical value that denotes the percentage of the total maximum length over which a signature should exist for it to be considered a potential noise signature.

It will be appreciated by those skilled in the art that there may be situations where the data is sparse and exists in isolated portions only. For these data types the variation in amplitude for weld signatures is not easily differentiable from the flaw signatures over their extents. Therefore, a second threshold (for example, Threshold 2 as given below) may be used to prevent flaw signature loss in these scans.

Threshold 2=0.4×Area

Where Area=(len×width)/(M×N) represents the extent of the region in the scan over which valid data is present and is the ratio of actual data area to the total area of the scan.
Width=maximum number of non zero rows in the scan
0.4 is an empirical value obtained from observations Using these thresholds and by comparing heights of amplitude responses with the first threshold, the presence of weld reflections is determined and approximate amplitude of the weld reflections is obtained. Multiple reference amplitude responses meeting the threshold criterion are selected from the identified weld reflections and are tagged as reference weld signatures.

It would be appreciated by those skilled in the art that the inherent in-homogeneity in the material results in increased scattering and absorption of the ultrasound signal with respect to distance traveled by the ultrasonic wave, thus the variation of amplitude increases with the distance traveled by the ultrasonic wave. Manufacturing defects during the welding process may also cause certain irregularities observed in the B-Scan (ultrasound scan data). To account for this disparity, an adaptive amplitude band that may be a unilateral band is drawn around the reference weld signatures as indicated in step 106 of FIG. 9. The adaptive amplitude band may vary non-linearly with respect to distance traveled within the material. Thus, to capture the entire length of the weld reflection, the histogram in the vicinity of the respective reference weld signature is checked using the adaptive amplitude band. In one example, a window of pre-determined width for example +400 nanosecond may be used to determine probable increase in the length of the weld signature. If the increase in length is more than 10% of the determined length, the signature is deemed valid and tagged as weld signature. After a signature is identified as a weld reflection the amplitudes within the unilateral band are tagged as weld signatures and may be suppressed or removed for obtaining a weld-suppressed image as indicated by step 108 of FIG. 9. Since, the removal/suppression operation is carried out only on the band, and there is a definite separation between flaw signatures and noise signatures in the histogram, the flaw pixels are left unchanged. This happens even if the flaw is embedded within the weld reflection such as cracks in the longitudinal weld of the material. This assumes that all flaw pixels will have an amplitude different from the approximate central amplitude value of the weld reflection.

At step 110 of FIG. 9, the method may additionally include using a noise filter for filtering noise in the weld-suppressed image to obtain a weld and noise suppressed image. The noise filtering removes isolated noise and any isolated weld reflections left behind in the weld-suppressed image. The noise observed is randomly scattered throughout the scan data. The noise may be due to inherent material in-homogeneity, ultrasound wave scattering and non-linear attenuation of the ultrasonic wave over its path of travel. In one example, the noise filter used at step 110 may be a multi-directional probabilistic filter with an adjustable width to capture noise in multi-directions. The noise may then be attenuated by using a transfer function in one example. Standard deviation may also be used as a pre-defined threshold to suppress noise. Since the amplitude responses may be irregular in nature and sparse over its extent, in one example, for noise filtering, all signatures greater than 60% of the minimum flaw length (along the horizontal direction) and all signatures greater than 40% of the flaw length in directions other than horizontal may be retained. This ensures the retention of 99.7% of the flaw pixels of interest. To simplify implementation, the filter width may be reduced proportionately to provide 40% signature retention in directions other than horizontal. It will be well appreciated by those skilled in the art that noise signatures will be of smaller length and will not meet the above criterion of flaw length and may easily be suppressed. The noise signatures may then be attenuated with a transfer function instead of being hard thresholded to zero. This enables reversibility in latter stages of the decision process, as the confidence on the weld versus flaw classification is relatively low in the first stage. By applying an inverse transfer function the original pixel values could be obtained if required. In one example, the transfer function [Q(x)was designed to operate in the range [255] window size and was computed as $$Q(x) = \exp^{P(x)/(k-1)}$$

Where $k=255/\log(1+R)$ $R=\max(X(i,j))$ $\forall$ $i=1:M$ and $j=1:N$ $X(i,j)$=pixel amplitude at ith row and jth column Further, due to the highly irregular shape and amplitude characteristics of the flaw signatures, additional filters may be designed by rotating the noise filter angularly for a particular angular range, for example within the limits +45° and −45°. These filters are non-overlapping in one example and the scan area covered is approximately 80% of the total area in which noise needs to be suppressed. The remaining 20% of the space may be oriented at angles greater than +57°. At these angles ultrasonic waves are typically unable to detect defects, as the flaw orientation is not favorable to reflections. The set of non-overlapping filters ensure that all signature segments are retained irrespective of their orientations and each filter responds only to one segment of the flaw signature.

It will be well understood by those skilled in the art that the responses corresponding to noise will have a similar response with respect to all the filters in the set, whereas flaw responses will have an anisotropic response with the proposed filter set. To filter the noise, the filter outputs may be stacked and the standard deviation (Stdev) may be calculated for the stacked filter output, as given below:

$$Stde(i, j) = \sqrt{\frac{1}{N}\sum_{s=1}^{k}(x_s(i, j) - \mu)^2}$$

Where i=Number of rows in the scan j=number of columns in the scan k=Number of filters/windows N=k μ=Mean pixel intensity across filters $$\mu = \frac{1}{N}\sum_{s=1}^{k} X_s(i, j)$$

In one example, the decision to suppress noise is based on the standard deviation. If the standard deviation is less than a predefined threshold then the noise signatures may be forced to zero.

At step 112 of FIG. 9, the method includes processing the weld and noise suppressed image to retrieve any flaw signature. This provides a technique to minimize the loss of flaw signatures. This step includes comparing the weld and noise suppressed image with the ultrasound scan data and estimating an approximate quantification of loss for flaw signatures. A threshold may be selected such that a minimum flaw length is recognized as a valid signature and is restored. An appropriate window size may be used based on scan parameters like minimum flaw size and measurement interval. A decision may then made on every sub-region of the scan as to whether there is a signature loss or not. Final image is thus devoid of most of the signatures that may give rise to false calls by other analysis algorithms used for post-processing the data.

It would be well appreciated by those skilled in the art that the foregoing flowcharts show the functionality and operation of the method and the apparatus for inspecting a pipeline. In this regard, each block/component represents a module, segment, or portion of code, which comprises one or more executable instructions for implementing the specified logical function(s). It should also be noted that in some alternative implementations, the functions noted in the blocks may occur out of the order noted in the figures or, for example, may in fact be executed substantially concurrently or in the reverse order, depending upon the functionality involved. Also, one of ordinary skill in the art will recognize that additional blocks may be added. Furthermore, the functions can be implemented in programming languages such as C++, MATLAB, or JAVA; however, other languages can be used.

The various embodiments and aspects of the invention described above may facilitate the creation of an ordered listing of executable instructions for implementing logical functions. Such an ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

It will also be well appreciated by those skilled in the art that the techniques described herein may be incorporated as algorithms, or could be implemented through hardware, for example, by using a programmed chip. Again, the algorithm or the hardware implementation may be incorporated in the PIG or may be a part of a remote processing system.

The aspects of the present techniques as described herein have several advantages over existing flaw detection techniques. Some of the advantages include enhancing flaw signatures by suppressing noise and weld signatures, decreasing the analysis time and increasing reliability and accuracy. The aspects of the techniques are particularly useful as these can be applied on discontinuous, sparse and irregular signatures. Experimental results included testing the false call rate on a sample set of 5 spool level files obtained from the PIG comprising approximately 100 boxes/areas (regions) where the false call rate came down from 82% to 7%, thus indicating the accuracy of the techniques employed herein. The aspects of technique described herein may also be customized for other non-destructive evaluation (NDE) modalities and applications by altering a few parameters.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for detecting weld signatures from ultrasound scan data obtained from scanning a pipeline, the method comprising:
    mapping a plurality of amplitude responses from the ultrasound scan data, each mapped amplitude response being representative of a respective sensor signal;
    locating a plurality of continuous amplitude responses from the plurality of mapped amplitude responses;
    locating a long weld angle co-ordinate from the continuous amplitude responses;
    identifying at least one corresponding signature for the continuous amplitude responses; and
    tagging the corresponding signature as a weld signature.

2. The method of claim 1 wherein locating the long weld angle co-ordinate comprises:
    selecting a first angularly oriented sensor corresponding to a first amplitude reflection signal close to a first surface of the pipeline; and
    selecting a second differently angularly oriented sensor adjacent to the first, that senses a second amplitude reflection signal close to the first surface of the pipeline.

3. The method of claim 2 further comprising computing the long weld angle co-ordinate from respective angular values of the first angularly oriented sensor and the second differently angularly oriented sensor.

4. The method of claim 1 further comprising mapping a plurality of signatures from the ultrasound scan data onto a three-dimensional histogram for locating the plurality of continuous amplitude responses.

5. The method of claim 4 further comprising using at least one pre-determined threshold for locating the continuous amplitude responses.

6. The method of claim 5 wherein the pre-determined threshold is at least one of length, standard deviation or spatial deviation of the mapped amplitude responses.

7. The method of claim 4 further comprising identifying at least one reference continuous amplitude response and a corresponding reference weld signature.

8. The method of claim 4 further comprising:
    selecting an adaptive band of a pre-determined width around the reference weld signature; and
    tagging the corresponding signatures in the adaptive band as weld signatures.

9. The method of claim 1 further comprising suppressing the weld signature and obtaining a weld-suppressed image.

10. The method of claim 9 further comprising using a noise filter for filtering noise in the weld-suppressed image to obtain a weld and noise suppressed image.

11. The method of claim 10 wherein the noise filter is a multi-directional probabilistic filter with an adjustable width to capture noise in multi-directions.

12. The method of claim 11 wherein the noise is attenuated by using a transfer function.

13. The method of claim 12 further comprising comparing standard deviation with a predefined threshold to suppress noise.

14. The method of claim 10 further comprising processing the weld and noise suppressed image to retrieve a flaw signature.

15. The method of claim 14 further comprising:
    comparing the weld and noise suppressed image with the ultrasound scan data; and
    estimating an approximate quantification of signal loss for flaw signatures.

16. The method of claim 15 further comprising selecting a threshold such that a minimum flaw length is recognized as a valid signature and restoring a corresponding signature.

17. An apparatus for identifying weld signatures from an ultrasound scan data, the apparatus comprising:
    an amplitude processing component for mapping a plurality of amplitude responses from the ultrasound scan data, and for locating a plurality of continuous amplitude responses, and for locating a long weld angle co-ordinate from the continuous amplitude responses, each mapped amplitude response being representative of a respective sensor signal; and
    a weld signature tagging component for identifying corresponding signatures for the continuous amplitude responses and for tagging the corresponding signatures as weld signatures.

18. An ultrasound imaging system used for detecting flaw signatures, the system comprising:
    a plurality of sensors disposed around a region of interest and configured to transmit and receive signals from the region of interest;
    a data acquisition system for acquiring ultrasound scan data from the plurality of sensors, the data being representative of signals received by the plurality of sensors from the region of interest;
    an amplitude processing component for mapping a plurality of amplitude responses from the ultrasound scan data, and for locating a plurality of continuous amplitude responses, each mapped amplitude response being representative of a respective sensor signal; and
    a weld signature tagging and suppressing component for identifying corresponding signatures for the continuous amplitude responses and for tagging the corresponding signatures as weld signatures, and for suppressing the weld signatures and obtaining a weld-suppressed image.

19. The imaging system of claim 18 further comprising a noise filter for filtering noise in the weld-suppressed image to obtain a weld and noise suppressed image.

* * * * *